United States Patent [19]

Gilbert et al.

[11] Patent Number: 4,724,100

[45] Date of Patent: Feb. 9, 1988

[54] LIQUID PHASE PROCESS FOR PRODUCING ESTERS

[75] Inventors: Robert M. Gilbert; Owen Portwood, both of Columbus; Gary W. Earl, Bexley, all of Ohio

[73] Assignee: Sherex Chemical Company, Inc., Dublin, Ohio

[21] Appl. No.: 844,441

[22] Filed: Mar. 26, 1986

[51] Int. Cl.[4] .......................... C11C 3/00; C07C 67/00

[52] U.S. Cl. ...................... 260/410.9 N; 260/410.9 R; 560/265

[58] Field of Search ................. 260/410.9 D, 410.9 N, 260/410.9 E, 410.9 R; 568/285; 560/265

[56] References Cited

U.S. PATENT DOCUMENTS

| | | | |
|---|---|---|---|
| 1,839,974 | 1/1932 | Lazier | 260/410.9 D |
| 3,180,898 | 4/1965 | Eisenlohr et al. | 260/638 |
| 3,853,986 | 12/1974 | Blass et al. | 423/659 |
| 4,152,278 | 5/1979 | Bell | 252/56 |
| 4,315,040 | 2/1982 | Heine et al. | 426/609 |
| 4,338,221 | 7/1982 | Qualeatti | 252/455 R |
| 4,340,546 | 7/1982 | Qualeatti et al. | 568/885 |
| 4,398,039 | 8/1983 | Pesa et al. | 560/265 |
| 4,405,819 | 9/1983 | Duckwall, Jr. | 568/814 |
| 4,446,073 | 5/1984 | Qualeatti et al. | 260/410.9 N |
| 4,480,115 | 10/1984 | McGinnis | 560/1 |

FOREIGN PATENT DOCUMENTS

| | | | |
|---|---|---|---|
| 0069946 | 1/1983 | European Pat. Off. . | |
| 1271701 | 7/1968 | Fed. Rep. of Germany ... | 260/410.9 N |
| 570957 | 7/1945 | United Kingdom . | |

OTHER PUBLICATIONS

Jojoba—National Research Council, National Academy Press, Washington, D.C., 1985, pp. 36–45, 68 and 69.

Boelhouwer et al., "Hydrogenation Selective de l'Acide Oleique en Alcool Oleylique", Chimie & Industrie, vol. 83, No. 6, Jun. 1960, pp. 875–881.

Pantulu et al., "Wax Ester Preparation by Reductive Esterification of Long-Chain Fatty Acids and by Synthesis", Journal of the Oil Technologists' Association of India, Jan.-Mar. 1972, pp. 9–14.

Shani, "Jojoba Oil and Some of Its Derivatives in Cosmetic and Health Products", Soap/Cosmetics/Chemical Specialties for Jul. 1983, pp. 42/44.

*Primary Examiner*—J. E. Evans

*Attorney, Agent, or Firm*—Pollock, Vande Sande & Priddy

[57] ABSTRACT

Esters are obtained from organic carboxylic acids and/or lower molecular weight esters thereof by a liquid phase reaction at temperatures of about 200° C. to about 350° C., pressures of about 50 psi to about 1800 psi, whereby water and/or alcohol by-product is removed during the reaction of the acid and/or lower molecular weight ester to the ester to thereby obtain the desired ester.

29 Claims, No Drawings

LIQUID PHASE PROCESS FOR PRODUCING ESTERS

DESCRIPTION

1. Technical Field

The present invention is concerned with a process for preparing esters from the corresponding organic carboxylic acid or ester of a lower molecular weight than the desired ester. In particular, the present invention is concerned with a liquid phase reductive condensation hydrogenation process for preparing self-esters employing relatively moderate pressures.

2. Background Art

Sperm whale oil and its derivatives, such as sulfurized sperm whale oil was an important additive for lubricants in view of its solubility and stability characteristics. However, since the sperm whale was added to the endangered species list in 1970, it became necessary to find replacements for the natural sperm oil. One such replacement suggested has been oleyl oleate which, according to the literature, is as good as or better than, sperm whale oil with regard to anti-wear testing, extreme pressure tests, and kinetic oiliness testing.

Sperm whale oil is composed mainly of about 35% triglycerides and about 65% fatty esters. The fatty esters are simple monoesters derived mainly from $C_{16}$ and $C_{18}$ alcohol with about 60% unsaturation and $C_{14}$, $C_{16}$, $C_{18}$, and $C_{20}$ carboxylic acids with about 75% unsaturation. The unsaturation is mainly mono-olefinic which is believed to contribute to the stability of the oil. During sulfurization, elemental sulfur and the oil are heated under inert atmosphere for several hours to provide a product containing thioether groups with an almost complete loss of unsaturation.

Furthermore, certain problems or disadvantages have been noted with respect to substitutes for natural jojoba oil.

For instance, a publication entitled "Jojoba", National Research Council, National Academy Press, Washington, D.C., 1985, includes a discussion of orange roughy oil and synthetic jojoba as substitutes for natural jojoba oil at page 68, et seq. In particular, orange roughy oil is described as C-36, C-38, and C-40 waxesters which is extracted from wastes of the orange roughy fishing industry. The oil is contaminated with up to 5% triglycerides plus some saturated and unsaturated fatty acids and fatty alcohols. The raw, unrefined oil is unusually corrosive, likely due to the free acid content.

Synthetic jojoba has been marketed by several chemical companies. However, to date, these alkyl esters are made by a process similar to that suggested in U.S. Pat. No. 4,152,278, discussed hereinbelow. Natural jojoba oil has two major chemical advantages over the synthetic variety. It is more pure and it contains a double bond in each of the acid and the alcohol parts of the molecule. The latter fact apparently lends greater oxidative stability to the jojoba molecules as compared to most other vegetable oils whose polyunsaturation leads to color and odor problems or even tar and gum formation.

The art is replete with suggestions of processes to prepare esters. However, many of these processes suffer from being fairly complicated and/or expensive and/or capable of producing only relatively low yields.

For instance, U.S. Pat. No. 4,152,278 to Bell suggests the preparation of wax ester by first partially hydrogenating soybean triglycerides, then saponifying the ester to the corresponding free fatty acids. A portion of these fatty acids was then hydrogenated at relatively high pressure to provide an alcohol which could be distilled. Finally, the fatty alcohol and the fatty acid obtained from the first step were reacted to give the desired fatty ester.

U.S. Pat. No. 4,315,040 to Heine suggests a classical esterification process for obtaining long-chain ester which requires complicated processing involving reducing an alcohol including removing unreacted alcohol by distillation, which adds significantly to the total expense of the process.

SUMMARY OF THE INVENTION

The present invention is concerned with a process for preparing esters from organic carboxylic acids or from esters of lower molecular weight than the desired esters.

In particular, the present invention is concerned with a liquid phase process which comprises subjecting the organic carboxylic acid and/or ester of lower molecular weight in a reaction zone to a temperature of about 200° C. to about 350° C. at a pressure of about 50 psi to about 1800 psi. The reaction is carried out in the presence of a catalytic amount of a hydrogenation-dehydrogenation catalyst. In addition, it is important to the success of the process to remove water or alcohol product of reaction from the reaction zone during the reacting of the acid or lower ester to the desired ester.

By the process of the present invention, it is possible to provide esters by a one-step process at relatively moderate pressures. Accordingly, the process of the present invention makes it possible to produce esters by an economical and efficient method. In addition, the process of the present invention only requires, as reactant feed, the carboxylic acid and/or ester of lower molecular weight than the desired ester. In other words, it is not necessary to employ an alcohol pursuant to the present invention to obtain the desired ester.

In addition, the process of the present invention makes it possible to obtain synthetic esters which do not suffer from the disadvantages noted with the substitutes for natural jojoba oil discussed hereinabove.

BEST AND VARIOUS MODES FOR CARRYING OUT INVENTION

The present invention is concerned with a process for preparing esters of an organic carboxylic acid. The preferred esters obtained by the process of the present invention can be referred to as symmetrical esters or self-esters. The process of the present invention is preferably directed to forming esters from organic carboxylic acids and/or esters having a lower molecular weight than the desired ester product. The carboxylic acids generally have from 4 to 22 carbon atoms, more preferably having from 12 to 22 carbon atoms, and most preferably having from 16 to 20 carbon atoms. The lower molecular weight ester reactant generally has 1–4 carbon atoms in the portion thereof corresponding to the alcoholic residue portion of the ester and preferably is a methyl or ethyl ester of the carboxylic acid. The carboxylic reactant feed can be a single acid, a single lower molecular weight ester, or mixtures of acids and/or of esters. In addition, the preferred aspects of the present invention are concerned with producing esters from saturated and/or from ethylenically unsaturated carboxylic acids and/or lower molecular weight esters thereof.

In accordance with the present invention, it is essential that water by-product and/or alcohol product of reaction be removed during the process in order to achieve the high yields of ester under the moderate pressure conditions employed. The water, which is a by-product of the reaction when an acid reactant is used and alcohol which is a by-product of the reaction when an ester reactant is used, can be removed by employing a sparge technique using a gas such as hydrogen. Also, if desired, the sparge gas near the end of the reaction can be an inert gas such as nitrogen. The sparge technique is preferably carried out by a continuous sparging of the reaction mixture. The sparge rate must be sufficient to prevent significant buildup of water and/or alcohol of the reaction. In a typical reaction containing about 500 to about 1000 grams of the carboxylic reactant, the sparge rate is usually at least about 2 standard cubic feet per hour of gas and preferably about 2 to about 10 standard cubic feet per hour of gas for a reaction vessel such as a 2 liter pressure vessel containing about 500 to about 1000 grams of reactants.

Another method for removing water during the reaction is a periodic venting procedure whereby periodically the reactor is vented to reduce the pressure, followed by repressurizing to the desired pressure at stated intervals. One particular venting procedure involves reducing the pressure by venting approximately every 30 minutes of the reaction period. The pressure during the venting is reduced at least by 100 psi, preferably by about 200 psi or more. The reduction in pressure can be carried out such that progressively lower pressures are achieved as the reaction proceeds towards completion.

For instance, when carrying out the reaction at about 600 psi, the initial venting can be to about 400 psi with repressurizing with a gas such as hydrogen, to 600 psi every 30 minutes until a relatively low acid value of about 40–100 is achieved. At this point, the next venting can be down to about 200 psi until an acid value of about 20–40 is reached, and then down to about 100 psi and then, finally, to atmospheric to obtain an acid value of about 10 or less. It is also desirable, once the pressure is vented to about atmospheric, to employ a nitrogen sparge to ensure maximum production of ester at this stage of the process.

The process is generally carried out at temperatures of about 200° C. to about 350° C. and preferably from about 250° C. to about 320° C.

The pressure employed is about 50 psi to about 1800 psi, more usually about 100 psi to about 600 psi, and preferably about 200 psi to about 600 psi.

The reaction is generally completed in about 2 hours to about 20 hours and more usually in about 3 hours to about 7 hours. The reaction with saturated carboxylic acids is somewhat faster than that with ethylenically unsaturated carboxylic acids.

In addition, the process is carried out in the presence of a catalytic amount of a hydrogenation-dehydrogenation catalyst. Suitable hydrogenation-dehydrogenation catalysts include mixtures of copper and cadmium which may be in the form of the hydroxide and/or carbonate.

When it is desired to maintain the unsaturation of the acid, the cadmium can serve to protect the unsaturated groups from being hydrogenated. When the object of the process is to obtain saturated esters, zinc in the form of, for instance, zinc acetate, can be employed instead of the cadmium. The catalyst is generally employed in amounts of about 0.25% to about 10% by weight, based upon the acid feed and preferably about 0.75% to about 5% by weight. The acid generally contains about 0.3% to about 3% by weight of copper and about 0.1% to about 3% by weight of cadmium or zinc.

Other catalysts known to effect esterification can be employed in accordance with the present invention. Examples of such include copper chromite; $Cu(OH)_2$; zinc acetate; ZnO; CrO on CdO with $Al_2O_3$ carrier; CuO/ZnO; and $CdNO_3/Cu(OH)_2$.

The process of the present invention usually provides yields of at least 85% and preferably at least about 90%.

The esters of the present invention are used for those same purposes as are esters obtained in the prior art.

In particular, the esters obtained by the present invention are especially suitable as replacements for whale oil and can be sulfurized to provide valuable lubricant additives as has been suggested in the prior art.

The following non-limiting examples are presented to further illustrate the present invention. All of the following examples use about 700 grams of carboxylic reactant and all of the sparge rates are based upon the amount of the carboxylic reactant.

EXAMPLE 1

Into a 2 liter pressure reactor fitted with stirrer and heating-cooling coils are introduced about 700 grams of oleic acid, about 7.21 grams of $Cu(OH)_2$, and about 3.01 grams of $Cd(OH)_2$.

A vacuum of about 30 mm is applied in order to remove air from the reaction vessel. After this, hydrogen is introduced into the reaction vessel in order to increase the pressure to about 400 psi. The reaction mass is then brought to a temperature of about 500° F. to about 570° F. A sparge employing hydrogen gas of about 2 standard cubic feet per hour is applied to the reaction mass to remove water formed from the reaction. This sparge rate is maintained for about the first 7½ hours of the reaction and then raised to about 4 standard cubic feet per hour for the next 2½ hours of reaction until completion. The reaction mass is maintained at about 500° F. to about 570° F. for about 10 hours. After this, the reaction mass is cooled to a temperature of about 200° F. The catalyst is then removed from the product by filtration.

The product contains about 80% by weight of the self-ester, about 5% by weight of the feed acid, and very little alcohol, as determined by infrared spectra.

EXAMPLE 2

Example 1 is repeated, except that the sparge rate is only about 1 standard cubic foot per hour. The product, after about 10 hours of reaction, contains about 49% by weight of the ester and about 51% by weight of the acid. This demonstrates the importance of having an adequate sparge rate during the reaction in order to obtain the maximum amount of ester desired.

EXAMPLE 3

About 700 grams of commercial grade oleic acid, about 7.21 grams of $Cu(OH)_2$, about 3.01 grams of $Cd(OH)_2$, and about 0.2–0.35 grams of lime are added to a reaction vessel. A vacuum of about 30 mm is applied in order to remove any air. Hydrogen is then introduced into the reaction vessel in order to raise the pressure to about 400 psi. The reaction mass is then heated to an elevated temperature of about 500° F. to about 570° F. The pressure is then adjusted to about 600 psi. The reaction vessel, after ½ hour of reaction, is then vented to a pressure of about 400 psi and then repressurized to about 600 psi with hydrogen. This venting is repeated every ½ hour. The reaction is continued for about 4½ hours whereby it is cooled to a temperature of about 180° F. to about 220° F. and then filtered in order to remove catalyst. The product contains about 80% by weight of ester and about 0.7% by weight of acid.

EXAMPLE 4

About 700 grams of commercial grade oleic acid, about 7.21 grams of $Cu(OH)_2$, and about 2.1 grams of $Cd(OH)_2$ are added to a reaction vessel. A vacuum of about 30 mm is applied in order to remove air. Next, hydrogen is introduced in order to raise the pressure to about 400 psi and the reaction mass is heated to a temperature of about 500° F. to about 540° F. The pressure is then adjusted to about 600 psi. After ½ hour the reaction vessel is vented to a pressure of about 400 psi and then repressurized to about 600 psi with hydrogen. This is repeated every ½ hour until the fourth hour of the reaction when the venting is down to 200 psi. At 4½ hours the venting is down to 100 psi, and then at 5 hours the reaction vessel is vented to the atmosphere and a nitrogen gas sparge of about 1 standard cubic foot per hour is initiated. In addition, after 6 hours of reaction the temperature is reduced to about 400° F. and the reaction is continued for another hour. After this, the reaction mass is cooled to about 200° F. and the catalyst is filtered out. The product contains about 94% by weight of oleyl oleate and about 0.4% by weight of acid. It is noted that after 5½ hours of reaction the product is analyzed and contains 98% by weight of ester and 0.2% by weight of the acid.

EXAMPLE 5

About 700 grams of a mixture of saturated carboxylic acids containing about 7% by weight of $C_{12}$ acids, about 21% by weight of $C_{14}$ acids, about 53% by weight of $C_{16}$ acids, and about 19% by weight of $C_{18}$ acid; about 4.69 grams of $Cu(OH)_2$ and about 7.7 grams of Zn acetate are added to a reaction vessel. A vacuum of about 30 mm is applied in order to remove any air. Hydrogen is then introduced into the reaction vessel in order to raise the pressure to about 400 psi and the reaction mass is heated to a temperature of about 540° F. The pressure is then adjusted to about 600 psi. After about ½ hour the reaction vessel is vented to a pressure of about 400 psi and then repressurized to 600 psi with hydrogen. This venting and repressurizing is repeated every ½ hour. The reaction is continued for about 3½ hours and then cooled to a temperature of about 180° F. to about 220° F. and then filtered in order to remove catalysts. The reaction product contains about 87% by weight of ester, about 2.5% by weight of alcohol, and about 0.01% by weight of acid.

EXAMPLE 6

About 700 grams of a carboxylic acid composition containing at least about 90% by weight of erucic acid, about 4.69 grams of $Cu(OH)_2$, and about 2.31 grams of $Cd(OH)_2$ are added to a reaction vessel. A vacuum of about 30 mm is applied in order to remove air. Next, hydrogen is introduced in order to raise the pressure to about 400 psi and the reaction mass is heated to a temperature of about 550° F. The pressure is then adjusted to about 600 psi. After about ½ hour the reaction vessel is vented to a pressure of about 400 psi and then repressurized to 600 psi with hydrogen. This venting and repressurizing is repeated every ½ hour.

The reaction is continued for about 3 hours, after which the reaction mass is cooled to a temperature of about 180° F. to about 220° F. and then filtered in order to remove any catalysts. The product contains about 89.8% by weight of ester, about 2.7% by weight of alcohol, and about 0.1% by weight of acid.

EXAMPLE 7

About 700 grams of a carboxylic acid mixture containing about 92% by weight of $C_{12}$ ethylenically unsaturated acid, about 5.6 grams of $CuCO_3$, and about 3.5 grams of $CdCO_3$ are added to a reaction vessel. A vacuum of about 30 mm is applied in order to remove air. Next, hydrogen is introduced in order to raise the pressure to about 400 psi and the reaction mass is heated to a temperature of about 540° F. The pressure is then adjusted to 600 psi. After ½ hour the reaction vessel is vented to a pressure of 400 psi and then repressurized to 600 psi with hydrogen. This venting and repressurizing is repeated every ½ hour. The reaction is continued for about 5½ hours, after which the reaction mass is cooled to a temperature of about 180° F. to about 220° F. and then filtered in order to remove catalysts. The product contains about 95.1% by weight of ester, about 1.8% by weight of alcohol, and about 0.1% by weight of acid.

EXAMPLE 8

About 700 grams of a mixture of saturated carboxylic acids containing about 85% by weight of $C_22$ acids, about 4.69 grams of $Cu(OH)_2$, and about 7.7 grams of zinc $(acetate)_2$ are added to a reaction vessel. A vacuum of about 30 mm is applied in order to remove air. Next, hydrogen is introduced in order to raise the pressure to about 400 psi and the reaction mass is heated to a temperature of about 550° F. The pressure is then adjusted to about 600 psi. After ½ hour the reaction vessel is vented to a pressure of 400 psi and then repressurized to 600 psi with hydrogen. This venting and repressurizing is repeated every ½ hour. The reaction is continued for about 2.5 hours, after which the reaction mass is cooled to a temperature of about 180° F. to about 220° F. and then filtered in order to remove catalysts. The product contains about 82.5% by weight of ester, about 11% by weight of alcohol, and about 0.5% by weight of acid.

EXAMPLE 9

About 700 grams of rape acids having an iodine value of about 98.2, about 6.23 grams of $CuCO_3$, about 3.5 grams of $CdCO_3$, and about 7 grams of lime are added to a reaction vessel. A vacuum of about 30 mm is applied in order to remove air. Next, hydrogen is introduced in order to raise the pressure to about 400 psi and the reaction mass is heated to a temperature of about 540° F. The pressure is then adjusted to about 600 psi. After about ½ hour the reaction vessel is vented to a pressure of about 400 psi and then repressurized to 600 psi with hydrogen. This venting is repeated every ½ hour. The reaction is continued for about 6 hours, after which the reaction mass is cooled to a temperature of about 180° F. to about 220° F. and then filtered in order to remove catalysts. The product contains about 91.9% by weight of ester, about 2.3% by weight of alcohol, and about 1.2% by weight of acid.

EXAMPLE 10

About 700 grams of stearic acids, about 4.69 grams of $Cu(OH)_2$, and about 2.31 grams of $Cd(OH)_2$ are added to a reaction vessel. A vacuum of about 30 mm is applied in order to remove air. Next, hydrogen is introduced in order to raise the pressure to about 400 psi and the reaction mass is heated to a temperature of about 540° F.

The pressure is then adjusted to about 600 psi. After about 1/2 hour the reaction vessel is vented to a pressure of about 400 psi and then repressurized to 600 psi with hydrogen. This venting and repressurizing is repeated every ½ hour. The reaction is continued for about 4 hours, after which the reaction mass is cooled to a temperature of about 180° F. to about 220° F. and then filtered in order to remove catalysts. The product contains about 81.6% by weight of ester, about 0.1% by weight of acid.

EXAMPLE 11

About 700 grams of tall oil acids, about 4.69 grams of $Cu(OH)_2$, and about 2.31 grams of $Cd(OH)_2$ are added to a reaction vessel. A vacuum of about 30 mm is applied in order to remove air. Next, hydrogen is introduced into the reaction vessel in order to raise the pressure to about 400 psi and the reaction mass is heated to a temperature of about 540° F. The pressure is then adjusted to about 600 psi. After about ½ hour the reaction vessel is vented to a pressure of about 400 psi and then repressurized to about 600 psi with hydrogen. This venting and repressurizing is repeated every ½ hour. The reaction is continued for about 7 hours, after which the reaction mass is cooled to a temperature of about 180° F. to about 220° F. and then filtered in order to remove catalysts. The product contains about 91.6% by weight of ester, about 2% by weight of alcohol, and about 0.2% by weight of acid.

EXAMPLE 12

About 700 grams of a mixture of ethylenically unsaturated acids containing about 90% by weight of $C_{16}$ acids, about 5.6 grams of $Cu(OH)_2$, and about 3.5 grams of $Cd(OH)_2$ are added to a reaction vessel. A vacuum of about 30 mm is applied in order to remove air. Next, hydrogen is introduced in order to raise the pressure to about 400 psi and the reaction mass is heated to a temperature of about 540° F. The pressure is then adjusted to about 600 psi. After about ½ hour of reaction, the reaction vessel is vented to a pressure of about 400 psi and then repressurized to about 600 psi with hydrogen. This venting and repressurizing is repeated every ½ hour. The reaction is continued for about 5 hours, after which the reaction mass is cooled to a temperature of about 180° F. to about 220° F. and then filtered in order to remove catalysts. The product contains about 87.2% by weight of ester, about 2.3% by weight of alcohol, and about 1.4% by weight of acid.

EXAMPLE 13

Into a reaction vessel are introduced about 700 grams of a mixture of oleic acid, about 4.69 grams of $Cu(OH)_2$, and about 2.31 grams of $Cd(OH)_2$ are added to a reaction vessel. A vacuum of about 30 mm is applied in order to remove air. After this, hydrogen is introduced into the reaction vessel in order to increase the pressure to about 400 psi. The reaction mass is then brought to a temperature of about 570° F. A sparge employing hydrogen gas of about 10 standard cubic feet per hour is applied to the reaction mass to remove water formed during the reaction. This sparge rate is continued for the duration of the reaction, which is about 6 hours. After about 2.5 hours of reaction the product has an acid value of about 24 and at that time the pressure is reduced to about 100 psi. After about 6 hours the reaction mass is cooled to about 100° F. The catalyst is then removed from the product by filtration.

The product contains about 98.3% by weight of the ester, about 0.4% of the feed acid, and very little alcohol.

EXAMPLE 14

Example 13 is repeated, except that the pressure is about 300 psi for the first about 3½ hours of reaction, at which time the product has an acid value of about 30 and the pressure is reduced to about 50 psi. The product obtained contains about 99.4% by weight of the ester and about 0.4% by weight of the feed acid.

EXAMPLE 15

Example 14 is repeated, except that the pressure throughout the entire reaction time is about 600 psi. The product obtained contains about 92.5% by weight of the ester and about 0.4% by weight of the feed acid.

EXAMPLE 16

Example 15 is repeated, except that the pressure for the reaction is about 1200 psi and the reaction is continued for about 8 hours. The product obtained contains about 93% by weight of the ester and less than 0.5% by weight of the feed acid.

EXAMPLE 17

Example 16 is repeated, except that the pressure for the first two hours of reaction is about 1200 psi and no sparge is employed. After 2 hours of reaction a sparge of hydrogen gas of about 10 standard cubic feet per hour is applied. After another 2 hours the pressure is reduced to about 100 psi and the reaction is continued for another 4 hours. The product obtained contains about 94% by weight of the ester and less than 0.5% by weight of the feed acid.

EXAMPLE 18

Example 17 is repeated, except that no sparge is employed and the reaction is continued for about 7 hours. The product obtained contains only about 18% by weight of the ester and about 37% by weight of the feed acid. This demonstrates the criticality of having a sparge or other means during the reaction in order to obtain the maximum amount of ester desired.

EXAMPLE 19

Into a reaction vessel are introduced about 700 grams of Emery 1016 dimer acid, about 9.4 grams of $Cu(OH)_2$, and about 4.6 grams of $Cd(OH)_2$. A vacuum of about 30 mm is applied in order to remove air from the reaction vessel. After this, hydrogen is introduced into the reaction vessel in order to increase the pressure to about 400 psi and the reaction mass is heated to about 540° F. The pressure is then adjusted to about 600 psi. After about ½ hour of reaction, the reaction vessel is vented to a pressure of about 400 psi and then repressurized to about 600 psi with hydrogen. This venting and repressurization is repeated every ½ hour. The reaction is continued for about 6.5 hours, after which the reaction mass is cooled to a temperature of about 180° F. to about 220° F. and then filtered in order to remove catalysts. The product contains about 75% by weight of ester and about 0.4% unreacted acid.

EXAMPLE 20

Into a reaction vessel are introduced about 700 grams of oleic acid, about 5.6 grams of $CuCO_3$, and about 3.5 grams of $CdCO_3$. A vacuum of about 30 mm is applied in order to remove air from the reaction vessel. After this hydrogen is introduced into the reaction vessel in order to increase the pressure to about 200 psi. The reaction mass is then brought to a temperature of about 570° F. A sparge employing hydrogen gas at a rate of about 10 standard cubic feet per minute is applied to the reaction mass in order to remove water from the reaction. After about 20 hours reaction time the reaction mass is cooled to a temperature of about 100° F. The catalyst is then removed from the product by filtration. The product contains about 81.3% by weight of the ester and about 0.4% by weight of the feed acid. The reaction is about 99.6% complete. The product removed from the reaction mass after about 16 hours of reaction contained 77% by weight of ester and about 14% by weight of the feed acid.

EXAMPLE 21

About 700 grams of oleic acid, about 5.6 grams of $CuCO_3$, and about 3.5 grams of $CdCO_3$ are added to a reaction vessel. A vacuum of about 30 mm is applied in order to remove air. Next, hydrogen is introduced in order to increase the pressure to about 400 psi and the reaction mass is heated to a temperature of about 570° F. The reaction vessel, after about ½ hour of reaction, is then vented to a pressure of about 100 psi and then repressurized to about 400 psi with hydrogen. This venting and repressurizing is repeated every ½ hour. The reaction is continued for about 10 hours. Thereafter, the reaction mass is cooled to about 180° F. to about 220° F. and then filtered in order to remove catalysts. The product contains about 78.8% by weight of ester and about 0.3% by weight of feed acid.

EXAMPLE 22

Into a reaction vessel are introduced about 700 grams of isostearic acid, about 5.6 grams of $CuCO_3$, and about 3.5 grams of $CdCO_3$. A vacuum of about 30 mm is applied to remove air from the vessel. Then hydrogen is introduced into the reaction vessel to a pressure of about 400 psi. The reaction mass is then brought to a temperature of about 540° F. The pressure is then adjusted to about 600 psi. After about ½ hour of reaction the reaction vessel is vented to a pressure of about 200 psi and then repressurized to about 600 psi with hydrogen. This venting and repressurizing is repeated every ½ hour. The reaction is continued for about 3½ hours, after which the reaction mass is cooled to a temperature of about 180° F. to about 220° F. and then filtered in order to remove catalyst. The product contains about 95% by weight of ester, about 1.1% by weight of fatty acid, and about 1.6% by weight of alcohol.

EXAMPLE 23

Into a reaction vessel are introduced 700 grams of tallow fatty acids (IV55), about 4.7 grams of $Cu(OH)_2$, and about 2.3 grams of Zn acetate. A vacuum of about 30 mm is applied to remove air from the vessel. Then hydrogen is introduced into the reaction vessel to a pressure of about 400 psi. The reaction mass is then brought to a temperature of about 540° F. The pressure is then adjusted to about 600 psi. After about ½ hour of reaction, the reaction vessel is vented to a pressure of about 200 psi and then repressurized to about 600 psi with hydrogen. This venting and repressurizing is repeated every ½ hour. The reaction is continued for about 3½ hours, after which the reaction mass is cooled to a temperature of about 180° F. to about 220° F. and then filtered in order to remove catalyst. The product contains about 87.3% by weight of ester, about 0.3% by weight of acid, and about 2.5% by weight of alcohol. The product ester has an IV of about 12.8. The lowering of the IV is due to the use of zinc in the catalyst instead of a material such as cadmium.

Having thus described our invention, what we claim as new and desire to secure by Letters Patent is:

1. A liquid phase process for preparing an ester from an organic carboxylic reactant from the group of organic carboxylic acid, an ester thereof having a lower molecular weight than the desired ester, or mixtures thereof which comprises:

subjecting said organic carboxylic reactant in a reaction zone to a temperature of about 200° C. to about 350° C. at a pressure of about 50 to about 1800 psi in the presence of a catalytic amount of hydrogenation-dehydration catalyst and removing water or alcohol product of reaction of said organic carboxylic reactant to said ester, achieving an acid value of about 10 or less and further provided that the pressure is below 200 psi after the acid value of the reaction mass reaches 20–40, and wherein said temperature of about 200° C. to about 350° C. is maintained, and thereby obtaining said ester in a yield of at least about 80%.

2. The process of claim 1 wherein said temperature is about 250° C. to about 320° C.

3. The process of claim 1 wherein the pressure is about 200 psi to about 1800 psi.

4. The process of claim 1 wherein the pressure is about 200 psi to about 600 psi.

5. The process of claim 1 wherein the water is removed by sparging a gas through the reaction mixture.

6. The process of claim 5 wherein the sparge rate is at least about 2 standard cubic feet per hour of a gas for about 500 to about 1000 grams of reactant.

7. The process of claim 5 wherein the sparge rate is about 2 to about 10 cubic feet per hour of a gas for about 500 to about 1000 grams of reactant.

8. The process of claim 5 wherein said gas includes hydrogen.

9. The process of claim 5 wherein near the end of the reaction said gas includes nitrogen.

10. The process of claim 1 wherein the water is removed by venting the reaction vessel in order to reduce the pressure by at least about 100 psi.

11. The process of claim 1 wherein the water is removed by venting the reaction vessel in order to reduce the pressure by at least about 200 psi.

12. The process of claim 11 wherein the pressure is reduced intermittently and repressurized approximately every 30 minutes of the reaction.

13. The process of claim 1 wherein said acid is an ethylenically unsaturated carboxylic acid.

14. The process of claim 1 wherein said acid contains from 4 to 22 carbon atoms.

15. The process of claim 1 wherein said acid contains from 12 to 22 carbon atoms.

16. The process of claim 1 wherein said acid contains from 16 to 20 carbon atoms.

17. The process of claim 13 wherein said acid contains from 12 to 22 carbon atoms.

18. The process of claim 13 wherein said acid contains from 16 to 20 carbon atoms.

19. The process of claim 1 wherein said acid is saturated carboxylic acid.

20. The process of claim 1 wherein said acid is dimer fatty acids.

21. The process of claim 1 which is conducted for about 2 to about 20 hours.

22. The process of claim 1 which is conducted for about 4 to about 10 hours.

23. The process of claim 1 wherein said catalyst contains a source of copper.

24. The process of claim 21 wherein said catalyst also contains a source of cadmium.

25. The process of claim 21 wherein said catalyst contains about 0.3% to about 3% by weight based upon the acid of said source of copper and about 0.1% to about 3.0% by weight based upon the acid of said source of cadmium.

26. The process of claim 21 wherein said catalyst also contains zinc and said ester is substantially saturated.

27. The process of claim 1 wherein the pressure is about 100 psi to about 600 psi.

28. The process of claim 1 wherein the pressure is about 200 psi after an acid value of about 40–100 is obtained, is reduced down to about 100 psi when an acid value of about 20–40 is reached, and is then reduced to about atmospheric pressure to obtain an acid value of about 10 or less.

29. The process of claim 28 which further comprises a nitrogen sparge and the pressure is reduced to about atmospheric pressure.

* * * * *